United States Patent
Mora-Fillat (10) Patent No.: US 8,920,750 B2
(45) Date of Patent: Dec. 30, 2014

(54) FLUIDIC CHIP WITH LAMINATED REINFORCING LAYER FOR PRESSURE REINFORCEMENT

(75) Inventor: Jose-Angel Mora-Fillat, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 176 days.

(21) Appl. No.: 13/409,937

(22) Filed: Mar. 1, 2012

(65) Prior Publication Data

US 2012/0251410 A1    Oct. 4, 2012

(30) Foreign Application Priority Data

Apr. 1, 2011    (GB) .................................. 1105529.0

(51) Int. Cl.
| | | |
|---|---|---|
| B01L 99/00 | (2010.01) | |
| B01J 20/285 | (2006.01) | |
| B01J 20/283 | (2006.01) | |
| B01L 3/00 | (2006.01) | |
| B01J 20/282 | (2006.01) | |
| G01N 30/60 | (2006.01) | |

(52) U.S. Cl.
CPC .. *B01L 3/502707* (2013.01); *B01J 2219/00824* (2013.01); *B01J 2219/00822* (2013.01); *B01L 2300/0887* (2013.01); *B01J 20/285* (2013.01); *B01J 2219/00808* (2013.01); *B01J 2219/00833* (2013.01); *B01L 2300/0816* (2013.01); *B01J 2219/00783* (2013.01); *B01J 20/283* (2013.01); *G01N 30/6095* (2013.01); *B01J 2219/00916* (2013.01); *G01N 30/6091* (2013.01); *B01J 20/282* (2013.01)
USPC ........................................ 422/503; 422/68.1

(58) Field of Classification Search
CPC ................. B01L 2300/0887; B01L 3/502707; B01J 2219/00783
USPC .......................................................... 422/503
See application file for complete search history.

(56) References Cited

U.S. PATENT DOCUMENTS

| | | | | |
|---|---|---|---|---|
| 4,636,331 | A | * | 1/1987 | Sako et al. .................... 252/511 |
| 5,344,703 | A | * | 9/1994 | Kovar et al. ................. 428/312.6 |
| 2002/0081222 | A1 | * | 6/2002 | Karp .............................. 417/507 |
| 2005/0040043 | A1 | * | 2/2005 | Stahler et al. ................. 204/450 |
| 2007/0251938 | A1 | * | 11/2007 | Lin et al. ..................... 219/443.1 |
| 2009/0074615 | A1 | | 3/2009 | Moles |
| 2009/0238722 | A1 | | 9/2009 | Mora-Fillat et al. |

FOREIGN PATENT DOCUMENTS

| | | |
|---|---|---|
| EP | 1876453 A1 | 1/2008 |
| GB | 2437844 A | 11/2007 |
| WO | 03068402 A1 | 8/2003 |
| WO | 2009129850 A1 | 10/2009 |

OTHER PUBLICATIONS

Search Report issued Aug. 9, 2011, by the United Kingdom Intellectual Property Office with regard to related Application No. GB1105529.0 (4 pages).

* cited by examiner

Primary Examiner — Paul Hyun (57) ABSTRACT

A fluidic chip device configured for processing a fluidic sample includes two outer boundary layers, and at least one reinforcing layer arranged between the two outer boundary layers and being at both of its opposing main surfaces laminated with directly adjacent layers to reinforce pressure resistance of the fluidic chip device by the lamination, in which at least a part of the layers of the fluidic chip device includes a hole forming at least a part of a fluidic conduit for conducting the fluidic sample under pressure.

20 Claims, 5 Drawing Sheets

Fig. 6

FLUIDIC CHIP WITH LAMINATED REINFORCING LAYER FOR PRESSURE REINFORCEMENT

BACKGROUND ART

The present invention relates to a fluidic chip device.

In liquid chromatography, a fluidic analyte may be pumped through a column comprising a material which is capable of separating different components of the fluidic analyte. Such a material, so-called beads which may comprise silica gel, may be filled into a column tube which may be connected to other elements (like a control unit, containers including sample and/or buffers). Part of such a chromatography arrangement may be integrated in a fluidic chip device.

US 2009/238722 discloses such a fluidic chip device configured for processing a fluidic sample, the fluidic chip device comprising a substrate comprising a fluidic conduit for conducting the fluidic sample under pressure, and two reinforcing structures between which the substrate is arranged, wherein the two reinforcing structures are connected to one another to reinforce pressure resistance of the substrate.

Operation of a liquid chromatography system may involve the application of a high pressure such as 1000 bar or more. This may be a challenge for the involved components of the liquid chromatography system.

DISCLOSURE

It is an object of the invention to provide an efficient fluidic chip device being appropriate for high-pressure application.

According to an exemplary embodiment of the present invention, a fluidic chip device is provided which is configured for processing a fluidic sample, the fluidic chip device comprising two outer boundary layers, and at least one reinforcing layer arranged between the two outer boundary layers and being at both of its opposing main surfaces laminated with directly adjacent layers to reinforce pressure resistance of the fluidic chip device by the lamination, wherein at least a part of the layers of the fluidic chip device comprises a hole forming at least a part of a fluidic conduit for conducting the fluidic sample under pressure.

According to another exemplary embodiment, a method of fabricating a fluidic chip device for processing a fluidic sample is provided, the method comprising arranging at least one reinforcing layer between two outer boundary layers, laminating the at least one reinforcing layer at both of its opposing main surfaces with directly adjacent layers to reinforce pressure resistance of the fluidic chip device by the lamination, and providing at least a part of the layers of the fluidic chip device with a hole forming at least a part of a fluidic conduit for conducting the fluidic sample under pressure.

In the context of this application, the term "processing" may particularly denote any process performed with the sample. This may include a mere conduction of the fluidic sample through the fluidic chip device (for instance when the fluidic chip device is a connection piece). It is however also possible that the processing is an active procedure such as a sample separation, for example using a chromatographic column or an electrophoresis separation unit.

In the context of this application, the term "main surface" may particularly denote one of the two opposing (and usually parallel) surfaces of a structure such as a sheet-like reinforcement layer which contribute a large majority (for instance together at least 80% or even at least 90%) of the entire surface of the reinforcing layer. In other words, the reinforcement layer may be a cuboid-like structure or a thin-layer substrate having a first extension, a second extension and a third extension (all being perpendicular to one another or relating to orthogonal axes), wherein the first extension and the second extension may be both at least three times, particularly at least five times, more particularly at least ten times, smaller than the third extension.

In the context of this application, the term "laminated" may particularly denote the result of the creation of a laminate by bonding sheets of material, particularly using a bonding material or bonding agent. Lamination may be performed so that a number of preformed layers are fixedly connected to one another with a direct contact between adjacent layers (with exception of a very thin layer of the bonding agent, if any) so that the layers cannot be separated from one another without destroying the stack of laminated layers. Such a fixed connection may be achieved by, for instance, gluing, pressing, welding, bonding, remelting and solidifying, or a chemical reaction.

In the context of this application, the term "directly adjacent layers" may particularly denote layers which are in proximate or immediate contact with one another, i.e. which have touching surface portions, which may be stacked or packaged. However, the skilled person will understand that a very thin liner or bonding agent is not considered to remove the property of bonded or laminated layers being directly adjacent.

In the context of this application, the term "hole" may particularly denote any recess in a physical body which may have any desired shape such as a circular, rectangular, polygonal, trapezoidal, etc., cross section or an oblong recess. Such a hole may be, for instance, a through hole or a blind hole. A hole axis may extend for example parallel or perpendicular to a main surface of the substrate. A hole may be a straight structure or may be curved.

According to an exemplary embodiment of the invention, a laminate is provided, in which at least one sandwiched reinforcing layer is integrated. Such a reinforcing layer can be specifically configured for achieving pressure stability as a consequence of the laminate connection between the at least one reinforcing layer and adjacent layers. It has turned out to be highly advantageous to have the reinforcing structures not or not only on top or bottom of the laminate, but buried within the layer stack, which on the one hand provides for a significantly improved reinforcement effect and at the same time allows the outer boundary layers to be designed specifically in accordance with their reinforcing function. In other words, there is basically no longer any limitation for the selection of the material of the boundary layers in exemplary embodiments, which may be freely selected for instance with regard to their sealing properties in relation to any movable member mounted on one of the boundary layers. Simultaneously, also the material of the reinforcing layer(s) integrated in the interior of the layer stack, can be selected independently and specifically in accordance with the desired reinforcing effect.

Particularly, a HPLC-chip with laminated metal layers for pressure reinforcement is provided. Even more specifically, plastic layers (such as polyimide layers) may be integrated as an inner core of the layer stack with surrounding reinforcing layers (for instance metal layers) for pressure reinforcement, which, in turn, are covered by the outer boundary layers. Particularly, in the field of HPLC, pressure limitations of pure plastic layer stacks, for instance limitations of 150 bar, can be overcome by integrating reinforcing layers in an interior of a multilayer chip. Such metal layers may be arranged at positions, in which no direct contact with an analyte is present or may be configured (for instance by a proper material selection and/or by coating) to be compatible with fluidic samples such as biological samples. Therefore, a laminate structure of processed polyimide foils with sandwiched reinforcement layers preferably of metal may allow to meet high pressure requirements of 600 bar, 1200 bar or more, while at the same time keeping the layer stack compact and fluid-tight.

Next, further exemplary embodiments of the fluidic chip device will be explained. However, these embodiments also apply to the method.

In an embodiment, the at least one reinforcing layer is laminated with the directly adjacent layers over an entire surface area of both of its main surfaces. Hence, laminating over the whole surface area, i.e. in a continuous two-dimensional way, allows to further improve the pressure stability.

In an embodiment, the at least one reinforcing layer is glued at both of its opposing main surfaces with the directly adjacent layers. By using a glue or an adhesive for the lamination of the reinforcing layer of both opposing sides thereof, a further improved layer sequence in terms of pressure stability is obtained. Examples for glue to be used for adhering the layers, particularly for adhering metallic reinforcing layers to plastic boundary and/or core layers are Polyimides, Fluorocarbons, Epoxies, pressure sensitive Silicones, Rubber-Phenolics, Acrylics, Polyesters.

In an embodiment, the at least one reinforcing layer is in direct contact with plastic material at both opposing main surfaces. It has turned out that plastic material, such as polyimide, which is highly preferably for microfluidic chips, can be properly laminated to the reinforcing layer(s) such as those made of metallic material, in a stable way.

In an embodiment, at least one of the at least two outer boundary layers comprises a hole forming part of the fluidic conduit. Thus, an external access to the fluid conduit can be achieved via at least one of the outer boundary layers.

In an embodiment, at least one of the at least one reinforcing layer comprises a hole forming part of the fluidic conduit. Therefore, it is also possible to conduct the fluid through a reinforcing layer(s). For this purpose, it is possible to form the reinforcing layer from a biocompatible material compatible with biological fluids analyzed with the fluidic chip. However, it is also possible that surface portions of reinforcing layers not being made of a biocompatible material are coated with a material, which is bio-compatible.

In an embodiment, the hole of the at least one of the at least one reinforcing layer and the hole of the at least one of the at least two outer boundary layers are aligned with one another to form together a straight part of the fluidic conduit. Therefore, the holes in the various layers may cooperate for forming together at least a straight part of the fluidic conduit.

In an embodiment, the fluidic chip device comprises at least two reinforcing layers each arranged between the two outer boundary layers and each being at both of its opposing main surfaces laminated with directly adjacent layers to reinforce pressure resistance of the fluidic chip device by the lamination. It has turned out that, providing a plurality of reinforcement layers further improves the pressure stability. For instance, an alternating sequence of plastic layers and reinforcing layers may be provided.

In an embodiment, the fluidic chip device comprises at least one further layer, particularly a plurality of further layers, arranged between the at least two reinforcing layers. Therefore, different reinforcing structures may be free of a direct contact to one another, so that one or more plastic layers or other functional layers may be sandwiched between the reinforcing layers, so as to safely provide pressure stability with regard to pressures of fluids conducted through fluidic conduits. The close spatial relation between such reinforcing layers and core layers sandwiched in between provide for a very direct impact on pressure robustness.

In an embodiment, at least one of the at least one further layer comprises a hole forming part of the fluidic conduit. Thus, also these intermediate layers may contribute to the formation of the fluidic conduit.

In an embodiment, the at least one further layer comprises a top layer, a bottom layer, and at least one intermediate layer sandwiched between the top layer and the bottom layer. It has turned out that a sequence of three such layers allows to be processed properly, so as to allow supply, separation and draining of fluid in these three layers.

In an embodiment, at least one of the at least one further layer is made of plastic, particularly of polyimide. However, other pressure stable biocompatible plastic materials are possible as well, although polyimide has turned out to be a particularly powerful material for microfluidic chips.

In an embodiment, the at least two reinforcing layers are provided separately and without direct physical connect to one another. Therefore, the fluidic chip device may be free of any interconnection structure which couples the various reinforcing layers, which thereby remain separate from one another and laminated to other non-reinforcing layers.

In an embodiment, the fluidic chip device comprises a fluidic valve configured for selectively connecting or disconnecting the fluidic conduit to a fluidic path and being mounted in direct contact to one of the at least two outer boundary layers. Providing such a fluid valve may require a fluid-tight sealing to a connected member when the fluidic valves is moved for switching purposes. In an embodiment, the outer boundary layers are different from the reinforcing structures, so that it is possible to design them specifically in accordance with a sealing behavior between the material of the movable valve and a material of the corresponding outer boundary layer.

In an embodiment, the fluidic valve comprises or consists of a ceramic material. Particularly with such a material, it would be a challenge to contact the ceramic with a metal layer so that the opportunity to connect the ceramic material to plastic boundary layers simplifies a fluid tight sealing between ceramic valve and plastic boundary layer.

In an embodiment, at least one of the at least two outer boundary layers comprises a hole forming part of the fluidic conduit, wherein the fluidic valve is arranged to selectively establish fluid communication between the hole and the fluidic path. For instance, the fluidic valve may be switchable between different operation modes, in which a fluid communication between hole and fluidic path may be selectively enabled or disabled. Therefore, the system can be fluidically controlled.

In an embodiment, the fluidic valve is a rotary valve configured for being rotated for selectively connecting or disconnecting the fluidic conduit to the fluidic path, the rotary valve rotating in sealed contact with material, particularly plastic material, of the one of the at least two outer boundary layers. For instance, such a fluidic valve may have multiple components, which are displaceable relative to one another, so as to selectively bring different fluidic sub-parts in alignment or out of alignment.

In an embodiment, at least one of the at least one reinforcing layer has a thickness in a range between approximately 25 µm and approximately 300 µm, particularly in a range between approximately 50 µm and approximately 200 µm, more particularly in a range between approximately 70 µm and approximately 120 µm. Therefore, already quite thin metal foils may be sufficient as reinforcing layers and already provide sufficient pressure stability, while at the same time keeping the fluidic chip device compact. This also results from the fact that sandwiching the reinforcing layers between other layers in laminated form provides for a specifically high robustness.

In an embodiment, each of the layers is a planar recessed sheet. When the layers are laminated together, they form a stack with planar side walls (formed by surfaces of the layers being different from the main surfaces), each side wall being formed by all of the layers together. Therefore, foils or thin sheet layers may be used having holes or grooves, which can be formed for instance by laser processing. Multilayer stacks of such perforated foils can be formed.

In an embodiment, a surface roughness of at least one of the at least one reinforcing layer and/or of at least one of the two outer boundary layers and/or of the at least one further layer in a range between approximately 0.1 µm and approximately 10 µm, particularly in a range between approximately 3 µm and approximately 5 µm. It has turned out to further improve the stability and adhesion strength between the various laminated layers, if the reinforcing layer and/or the outer boundary layers are slightly roughened at their surfaces prior to the lamination.

In an embodiment, at least one of the at least one reinforcing layer is a plate. This plate may be so thin that it forms a sheet- or foil-like structure.

In an embodiment, a shape and a surface area of the two outer boundary layers match to a shape and to a surface area of the at least one reinforcing layer. For instance, it is possible to use foils or sheets with rectangular main surfaces having identical area and lengths for the outer boundary layers as well as for the reinforcing layers, and optionally for further layers (such as core layers).

In an embodiment, the at least one reinforcing layer has a thickness which differs by less than approximately 30%, particularly by less than approximately 20%, more particularly by less than approximately 10%, from a thickness of at least one of the two outer boundary layers. Therefore, the reinforcing effect can already be achieved by relatively thin reinforcing layers due to the lamination of these reinforcing layers in an interior of the layer stack. It can even be so that the reinforcing layers are thinner than the outer boundary layers.

In an embodiment, the at least one reinforcing layer has a mechanical resistance being larger than a mechanical resistance of the two outer boundary layers. The mechanical resistance is a property of the material used for the reinforcing layers as compared to the outer boundary layers and may indicate up to which force or pressure the corresponding layer remains intact to withstand the force or pressure.

In an embodiment, at least one of the two outer boundary layers has a thickness in a range between approximately 25 µm and approximately 300 µm, particularly in a range between approximately 50 µm and approximately 200 µm, more particularly in a range between approximately 70 µm and approximately 120 µm. Therefore, also the outer boundary layers may be very thin foils or thin-film substrates.

In an embodiment, at least one of the at least one reinforcing layer comprises at least one of a metal and a hard plastic. For example, the reinforcing layers may be made of stainless steel, while polyaryletherketone (PAEK) can be another suitable material for the reinforcing layers as well in certain application. Polyetheretherketone (PEEK) is a specific example for a plastic which might be used. The use of ceramic materials such as silicon carbide, aluminum oxide, magnesium oxide, etc. for the reinforcing layer(s) is possible as well.

In an embodiment, all layers form a stack of layers in which each adjacent pair of layers is connected to one another by lamination. Therefore, the fluidic chip device may consist of a laminate with one or more fluidic components integrated therein. Such a fluidic component integrated therein may for instance be a miniature chromatographic column.

In an embodiment, at least one of the at least two outer boundary layers comprises a top layer and a bottom layer. Therefore, also the outer boundary layers may be double layers or even multiple layers having three or more sublayers. Therefore, also complex structures with a sophisticated function may be established.

In an embodiment, at least one of the two outer boundary layers comprises or consists of at least one of a plastic, a polymer, a metal, a semiconductor, and a ceramic. However, it may be preferred that the outer boundary layers are made from plastic material such as polyimide as well.

In an embodiment, each of the two outer boundary layers has one main surface which is at least partially uncovered and exposed to an environment. These main surfaces of the two outer boundary layers may form the outer surfaces of the entire layer stack.

In an embodiment, the at least one reinforcing layer is laminated at one of its main surfaces to one of the at least two outer boundary layers. Therefore, it is possible that there is a direct contact between the outer boundary layers and the reinforcing structure or structures.

In an embodiment, the at least one reinforcing layer is laminated at one of its main surfaces to an intermediate layer arranged between the at least one reinforcing layer and the one of the at least two outer boundary layers. Such intermediate layers may be formed for performing specific tasks.

In an embodiment, the fluidic conduit is part of the fluidic chip device. For example, the fluidic chip device may be a HPLC chip through which a fluidic sample is conducted and separated by a chromatographic column.

In an embodiment, the fluidic chip device comprises a processing element arranged in the fluidic conduit and configured for interacting with the fluidic sample. Such a processing element may be a chromatographic column, integrated in the layer stack.

At least a part of a processing element provided in the substrate may be filled with a fluid separating material. Such a fluid separating material which may also be denoted as a stationary phase may be any material which allows an adjustable degree of interaction with a sample so as to be capable of separating different components of such a sample. The fluid separating material may be a liquid chromatography column filling material or packing material comprising at least one of the group consisting of polystyrene, zeolite, polyvinylalcohol, polytetrafluorethylene, glass, polymeric powder, silicon dioxide, and silica gel. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 µm to essentially 50 µm. Thus, these beads may be small particles which may be filled inside the separation column. The beads may have pores having a size in the range of essentially 0.008 µm to essentially 0.03 µm. The fluidic sample may be passed through the pores, wherein an interaction may occur between the fluidic sample and the pores. By such effects, separation of the fluid may occur.

The fluidic chip device may be configured as a fluid separation system for separating components of the mobile phase. When a mobile phase including a fluidic sample is pumped through the fluidic chip device, for instance with a high pressure, the interaction between a filling of the column and the fluidic sample may allow for separating different components of the sample, as performed in a liquid chromatography device or in a gel electrophoresis device.

However, the fluidic chip device may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The fluidic chip device may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic chip device may be or may be implemented in different technical environments, like a sensor device, a test device for testing a device under test or a substance, a device for chemical, biological and/or pharmaceutical analysis, a capillary electrophoresis device, a liquid chromatography device, a gas chromatography device, an electronic measurement device, or a mass spectroscopy device. Particularly, the fluidic chip device may be a High Performance Liquid Chromatography (HPLC) device by which different fractions of an analyte may be separated, examined and analyzed.

The fluidic chip device may be configured to conduct a liquid mobile phase through the processing element and optionally a further processing element. As an alternative to a liquid mobile phase, a gaseous mobile phase or a mobile phase including solid particles may be processed using the fluidic chip device. Also materials being mixtures of different phases (solid, liquid, gaseous) may be analyzed using exemplary embodiments.

The fluidic chip device may be configured to conduct the mobile phase through the processing element(s) with a high pressure, particularly of at least 600 bar, more particularly of at least 1200 bar. In the context of such a high pressure application, the corset function of the interconnected reinforcing arrangement may be particularly of interest.

The fluidic chip device may be configured as a microfluidic chip device. The term "microfluidic chip device" may particularly denote a fluidic chip device as described herein which allows to convey fluid through microchannels having a dimension in the order of magnitude of $\mu m$ or less.

The fluidic chip device may be configured as a nanofluidic chip device. The term "nanofluidic chip device" may particularly denote a fluidic chip device as described herein which allows to convey fluid through microchannels having a dimension in the order of magnitude of nm or less.

The fluidic chip device may be configured as a workflow integration system being configured for performing a predefined sequence of processes in accordance with a workflow to be executed. Such a workflow integration system may have one or multiple (for instance three, four or more) columns. Workflows may imply one or more processes previous to the separation such as column enrichment, digestion, etc.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

The illustration in the drawing is schematically.

Figure 6:
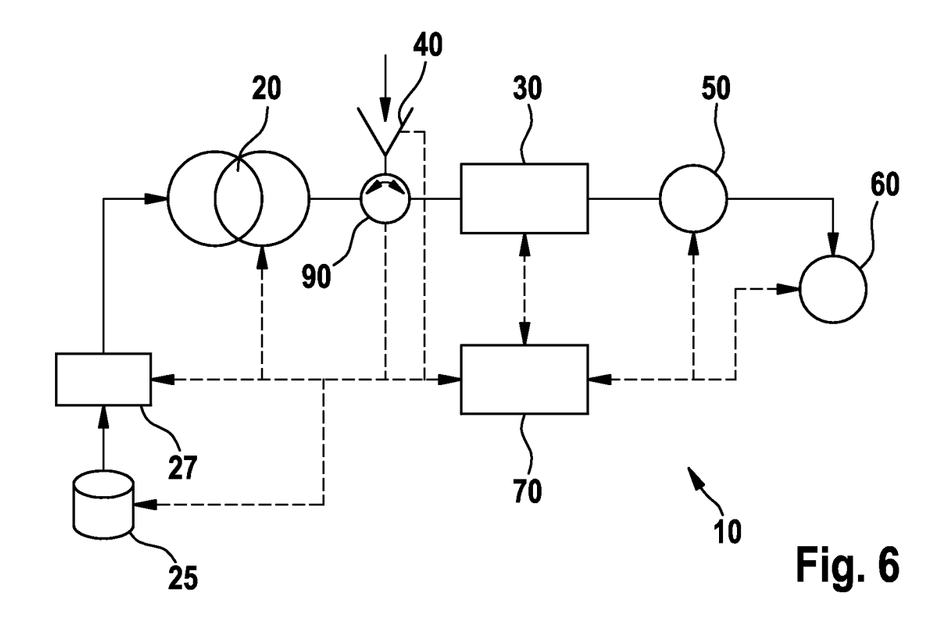
FIG. 6 shows a liquid separation device, in accordance with embodiments of the present invention, e.g. used in high performance liquid chromatography (HPLC).

Referring now in greater detail to the drawings, FIG. 6 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 (having a needle/seat arrangement depicted in FIG. 6 schematically) is provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump). The data processing unit 70 might also control operation of the solvent supply 25 (e.g. setting the solvent's or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization sample injection with operating conditions of the pump 20). A switchable valve 90 can be operated so as to adjust a desired fluidic coupling within the liquid separation system 10. The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provides data back.

A switchable valve 90 can be operated so as to adjust a desired fluidic coupling within the liquid separation system 10.

In the following, multiple embodiments of the invention related to metal chip reinforcement layers will be explained.

One of the challenges of HPLC chip/mass-spectroscopy devices is the pressure stability of the microchannels which form the hydraulic paths necessary to meet the demanding requirements regarding pressure stability of these devices. A HPLC chip/mass-spectroscopy device may use polyimide foils as a core surrounded by metal reinforcing layers. It is possible to realize such a metal reinforcement by providing for example two foils of stainless steel 304L of 100 μm thickness, which are laminated for reinforcing the core of the chip made of polyimide foils. As a result of this reinforcement, such a chip may have for instance nine layers (see FIG. 5), wherein for example two layers embedded in an interior of the layer stack may be made of a metal. To obtain a good adhesion between metal and polyimide, it is possible to adjust a surface roughness $R_a$ preferably in a range between 3 μm and 5 μm (although other roughness values may still be possible). The metal surfaces may be cleaned, using chemical cleaners in ultrasonic baths. It is also possible to perform a plasma treatment of the metal surfaces to promote adhesion. In other words, surfaces to be laminated may be activated or functionalized before lamination. In an embodiment, it is possible to use a material combination with different mechanical properties to obtain a package to form a high pressure chip, i.e. a chip having pressure stability.

In the following, referring to FIG. 1, a fluidic chip device 100 according to an exemplary embodiment will be explained.

Figure 1:
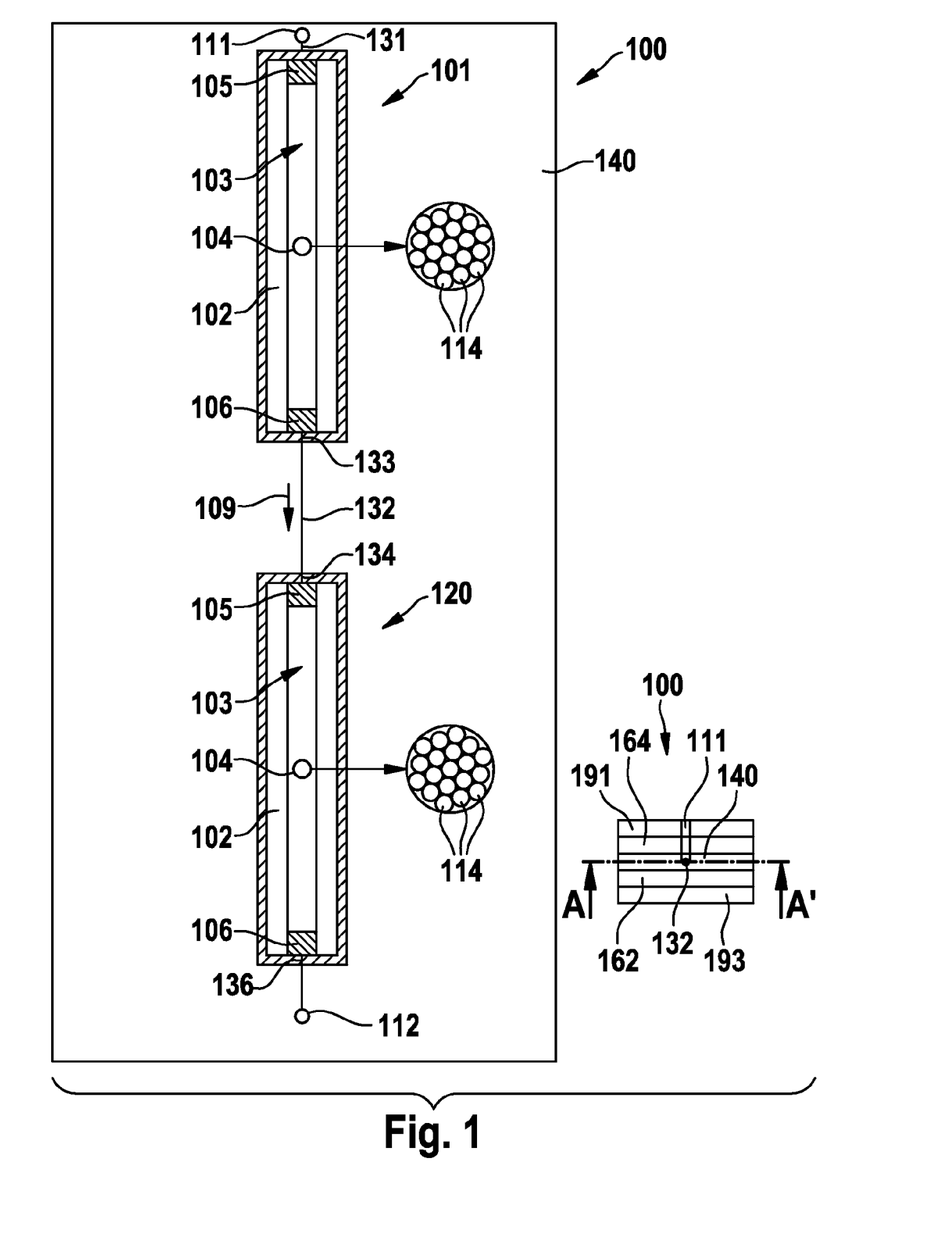
FIG. 1 illustrates a cross-section of a fluidic chip device according to an exemplary embodiment of the invention and also shows a side view of the corresponding layer stack.

The larger image in FIG. 1 shows a functional, processed polyimide core layer 140 of a multi-layer stack of the fluidic chip device 100. The smaller image in FIG. 1 shows a side view of the entire multi-layer stack of the fluidic chip device 100 which shows core layer 140 embedded between other layers, as will be described below in further detail.

The fluidic chip device 100 is adapted as a system for carrying out liquid chromatography investigations. The fluidic chip device 100 for separating different components of a fluid or a mobile phase which can be pumped through the apparatus 100 comprises a pre-column 101 for pre-processing (for instance sample preparation or sample enrichment) the fluidic sample and comprises an analytical or main column 120 for post-processing the fluidic sample which has already passed the pre-column 101. In other words, the system 100 is a two-stage fluid separation system. Other embodiments may include only a one-stage fluid separation system having only one column, or a multi-stage fluid separation system or a workflow integration system having multiple (for instance three, four or more) columns. Workflows imply the processes previous to the separation as: column enrichments, digestions, etc.

In the embodiment of FIG. 1, each of the fluid separating columns 101, 120 comprises a column tube 102 which is shaped to define closed packed channels, for instance having a rectangular cross-section. Within each of these fluid separating columns 101, 120, a tubular reception 103 is defined which is filled with a package composition 104.

The fluidic chip device 100 is adapted as a liquid chromatography device 100 and has, in each of the columns 101, 120, a first frit 105 close to an inlet 131, 134 of the respective columns 101, 120, and a second frit 106 provided at an outlet 133, 136 of the respective column 101, 120. The first frit 105 forms the inlet of the respective column 101, 120 and is provided upstream the respective column tube 102. The second frit 106 forms the outlet of the respective column 101, 120 and is located downstream of the respective column tube 102. A flowing direction of the fluid which is separated using the fluidic chip device 100 is denoted with the reference numeral 109.

A fluid pump (not shown) is provided externally from the chip 100 and pumps fluid under pressure of, for instance, 1000 bar through a connection tube or fluidic conduit 111 (extending perpendicular to the paper plane of FIG. 1) and from there to the inlet 131 of the pre-column 101, through the first frit 105 into the column tube 102. After having left the column tube 102, that is to say after having passed the second frit 106, an intermediate tube 132 connected to an outlet 133 of the pre-column 101 transports the pre-processed analyte to the inlet 134 of the main column 120. The internal construction of the main column 120 is similar to that of the pre-column 101, but may (or may not) differ from the pre-column 101 with respect to size and fluid separating material 114 filled in the tubular reception 103.

In a further stage, the sample is further separated in the main column 120, and the further separated sample leaves the outlet 136 of the main column 120. After having left the column tube 102 of the main column 120, that is to say after having passed the second frit 106 of the main column 120, a second fluidic conduit 112 (extending perpendicular to the paper plane of FIG. 1) transports the separated analyte to a container and analysis unit (not shown) positioned outside of the chip 100. The container and analysis unit includes cavities or containers for receiving different components of the fluid, and may also fulfill computational functions related to the analysis of the separated component(s).

The column tubes 102 comprise the filling 104. In other words, a packing composition 104 comprising a plurality of silica gel beads 114 is inserted into the hollow bore 103 of the column tube 102 of each of the columns 101, 120.

The mobile phase is first conducted through the pre-column 101. By selecting an appropriate ACN concentration in a $H_2O$ environment, a fraction of the fluidic sample may first be trapped at a particular position within the column tube 102 of the pre-column 101. This procedure may be denoted as a pre-focusing or pre-separation. Components of the mobile phase which are not trapped in the pre-column 101 are collected in a waste unit (not shown).

Afterwards, the ACN/H$_2$O concentration ratio within the column tube 102 of the pre-column 101 may be selectively modified so as to elute the sample trapped in the column tube 102 of the pre-column 101. Then, the fluidic sample will move through the outlet 133 of the pre-column 101, and will enter the inlet 134 of the main column 120 to be trapped in a portion close to the outlet of the frit 105 of the main column 120.

When the fluid passes through the main column 120, components which differ from a fraction to be separated may simply pass through the column 120 without being trapped and may be collected in a waste (not shown). At the end of this procedure, a band of the fraction of the fluidic sample of interest is trapped at a particular position within the main column 120. By again modifying the concentration ratio ACN/H$_2$O, for instance by gradually modifying the respective contributions of these two components, the trapped sample may be released from the main column 120 and may be conducted to another fluidic member for further processing.

Layer 140 in FIG. 1 is so to say the active layer of the layer stack, in which a plurality of the fluid separation procedures are carried out. However, the side view of the layer stack 100 shown in FIG. 1 as well illustrates that two outer boundary layers 191, 193 form the outer layers of the layer stack and are made from a plastic material such as polyimide. Sandwiched between the active layer 140 and one of the outer boundary layers 191, 193 is a respective one of two reinforcing metal layers 162, 164, for instance made of stainless steel. Each of the layers 193, 162, 140, 164, 191 is laminated on both of its opposing main surfaces (the large view of FIG. 1 shows one main surface of the active layer 140) with main surfaces of adjacent layers over the entire area of the main surfaces (outer boundary layers 191 and 193 are the only ones in which only one of the two main surfaces are laminated, the other one is exposed) by applying glue or adhesive and connecting them by applying some pressure. As a result of this lamination process, it is possible to obtain a very robust layer stack, which is capable of withstanding pressure values of 600 bar, 1200 bar or even more. High pressure values may be present in the channels 111, 132, 112 during a HPLC analysis. The layers 191, 164 and 140 comprise recesses or holes or channels, which together form the fluidic conduit 111 (layers 191, 164 and 140, see FIG. 1), the fluidic conduit 132 (only in layer 140) and the fluidic conduit 112 (again in layers 191, 164, 140). Therefore, these recesses or holes or channels may be in alignment to one another, so as to form together a fluidic path of the fluidic chip device 100.

Figure 2:
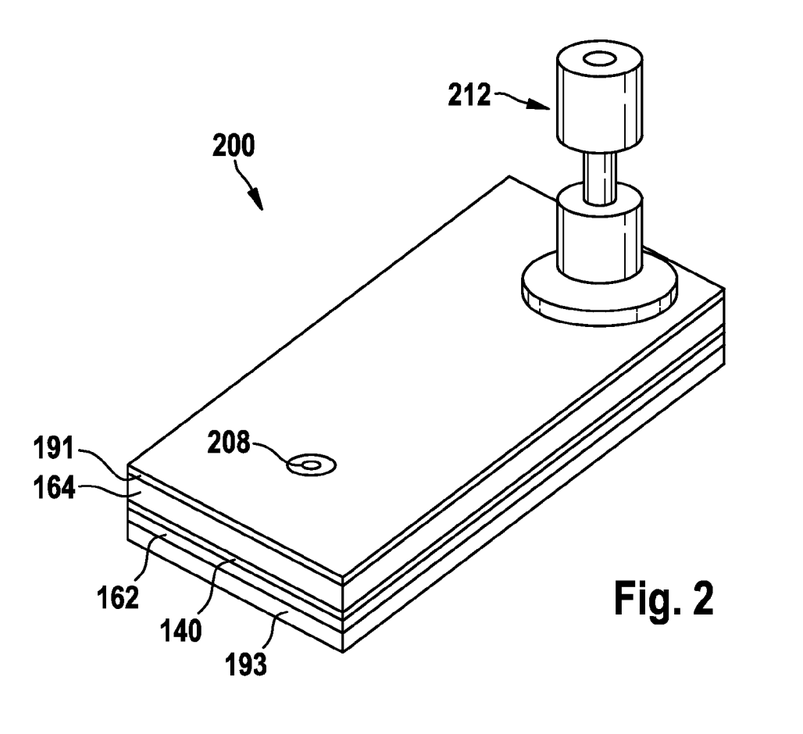
FIG. 2 illustrates a HPLC chip according to an exemplary embodiment of the invention having a rotary valve mounted thereon.

FIG. 2 shows a fluidic chip device 200 according to another exemplary embodiment of the invention in which a layer sequence similar to FIG. 1 is shown. A fluid supply opening (not shown) of the upper boundary layer 191 is covered by a rotary valve 212 of ceramic material, which is coupled to the layer stack, so as to provide a fluidic valve for supplying a fluid from an exterior position to the fluidic path of the layer stack. The rotary valve 212 can be switched by a rotation motion so as to selectively enable or disable fluid communication between the external fluid sample source and the fluidic path in the layer stack. Reference numeral 208 shows a drain hole via which the processed fluid can be drained after being processed particularly in layer 140.

It is important that the sealing between the ceramic material of the rotor valve 212 and the material of a directly contacted layer, i.e. upper boundary layer 191 is fluid-tight. Since the upper boundary layer 191 can be made of a plastic material such as polyimide, a proper sealing connection between material of the rotary valve 212 and material of the upper boundary layer 191 is possible.

Figure 3:
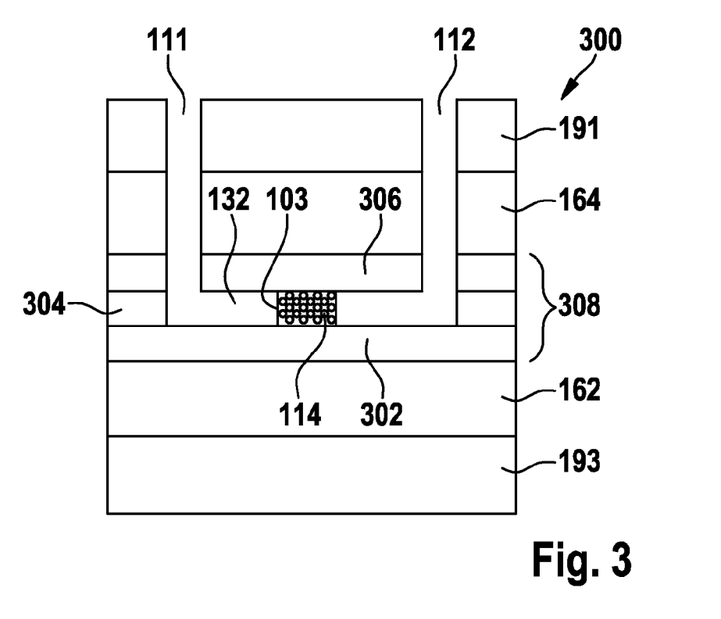
FIG. 3 illustrates a cross-section through a layer stack of a fluidic chip device according to an exemplary embodiment of the invention.

FIG. 3 shows cross-sectional view of a fluidic chip device 300 according to another exemplary embodiment of the invention, in which various layers are laminated together. The layer constitution is similar as in FIG. 1, but the detailed arrangement of the fluidic conduits 111, 112 can be better seen in FIG. 3. Furthermore, a core layer sequence 308 is sandwiched between the metal reinforcing layers 162 and 164 and is divided in three sub-layers in FIG. 3, which are denoted with reference numeral 302, 304 and 306. The upper layer 306, the lower layer 302 and the intermediate layer 304 are recessed and patterned and are sandwiched between the reinforcing layers 162, 164 so as to obtain a proper pressure stability.

Figure 4:
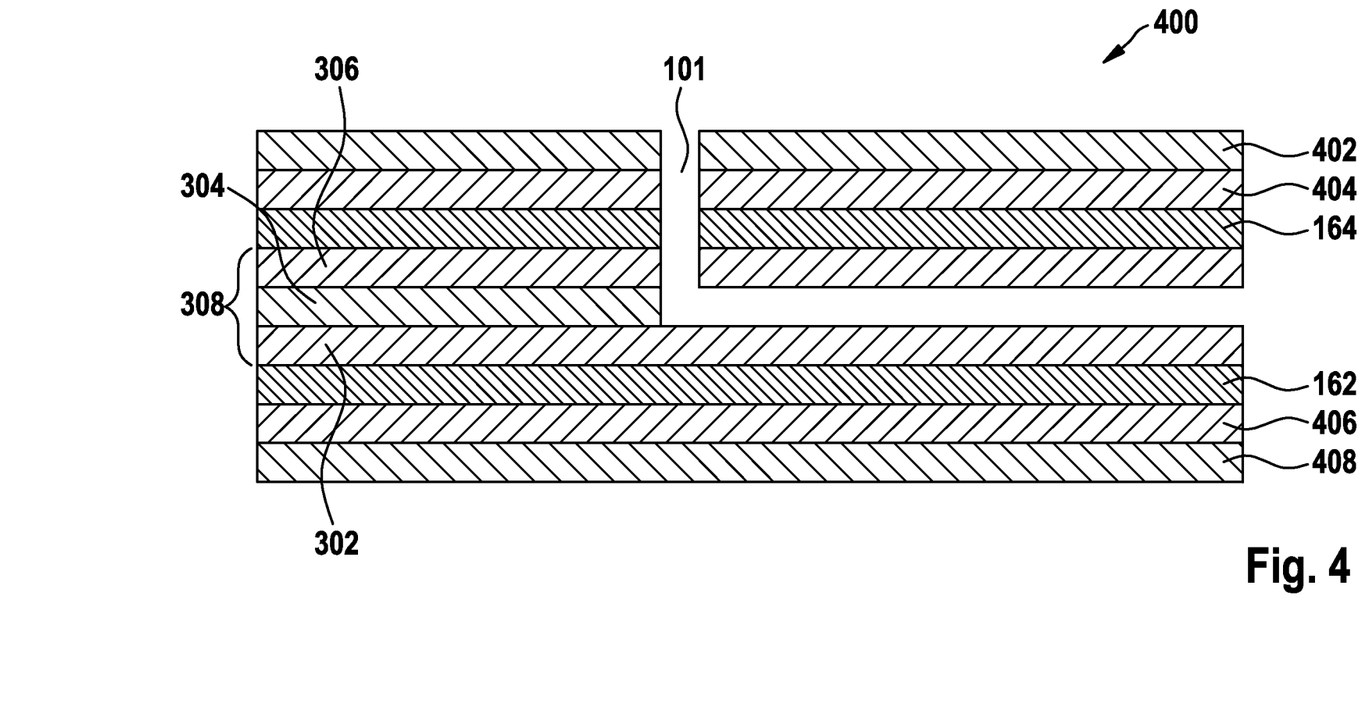
FIG. 4 schematically illustrates a cross-section of a layer stack of a fluidic chip device according to an exemplary embodiment of the invention.

FIG. 4 shows a cross-sectional view of a layer stack of a fluidic chip device 400 according to another exemplary embodiment again illustrating a layer sequence, in which however the upper boundary layer has two sub-layers 402, 404 and the lower boundary layer has two sub-layers 406 and 408.

Figure 5:
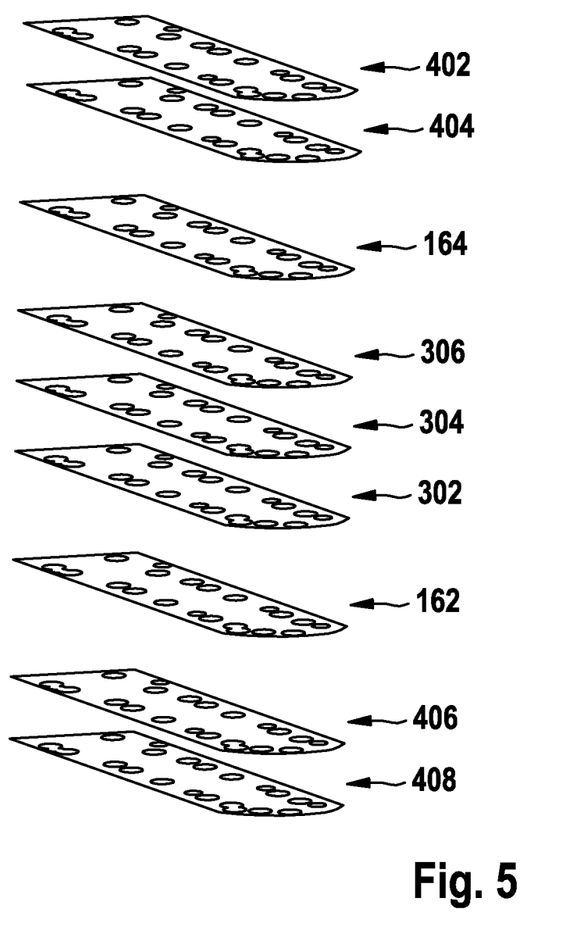
FIG. 5 shows an exploded view of a fluidic chip device having nine separate layers which are aligned for connection by lamination so as to form a layer stack as a fluidic chip device according to an exemplary embodiment of the invention.

FIG. 5 shows nine layers in the form of recessed sheets or foils, which are to be laminated together, so as to form a fluidic chip device similar to the one shown in FIG. 4.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A fluidic chip device configured for processing a fluidic sample, the fluidic chip device comprising:
   two outer boundary layers;
   at least two reinforcing layers arranged between the two outer boundary layers and each being at both of its opposing main surfaces laminated with directly adjacent layers to reinforce pressure resistance of the fluidic chip device by the lamination, the at least two reinforcing layers having a mechanical resistance larger than a mechanical resistance of the two outer boundary layers; and
   a core layer arranged between the at least two reinforcing layers, wherein the core layer is laminated with at least one of the at least two reinforcing layers, and comprises a hole forming at least a part of a fluidic conduit for conducting the fluidic sample under pressure.

2. The fluidic chip device according to claim 1, wherein at least one of the at least two reinforcing layers is laminated with the directly adjacent layers over an entire surface area of both of its main surfaces.

3. The fluidic chip device according to claim 1, wherein at least one of the at least two reinforcing layers is glued at both of its opposing main surfaces with the directly adjacent layers.

4. The fluidic chip device according to claim 1, wherein at least one of the at least two reinforcing layers is in direct contact with plastic material at both opposing main surfaces.

5. The fluidic chip device according to claim 1, wherein at least one of the two outer boundary layers comprises a hole forming part of the fluidic conduit.

6. The fluidic chip device according to claim 1, wherein at least one of the at least two reinforcing layers comprises a hole forming part of the fluidic conduit.

7. The fluidic chip device according to claim 6, wherein at least one of the two outer boundary layers comprises a hole forming part of the fluidic conduit, and the hole of the at least one of the two reinforcing layers and the hole of the at least one of the two outer boundary layers are aligned with one another to form together a straight part of the fluidic conduit.

8. The fluidic chip device according to claim 1, wherein the core layer is directly adjacent to and laminated with both of the at least two reinforcing layers.

9. The fluidic chip device according to claim 1, wherein the core layer comprises a plurality of core layers laminated together.

10. The fluidic chip device according to claim 1, wherein the core layer comprises a top layer, a bottom layer, and at least one intermediate layer sandwiched between the top layer and the bottom layer.

11. The fluidic chip device according to claim 1, wherein each of the layers is a planar recessed sheet, which layers, when laminated together, form a stack with planar side walls, each side wall being formed by all of the layers together.

12. The fluidic chip device according to claim 1, comprising a layer having a surface roughness in a range between 0.1 µm and 10 µm, the layer having the surface roughness being selected from the group consisting of: at least one of the at least two reinforcing layers, at least one of the two outer boundary layers, core layer, and a combination of two or more of the foregoing.

13. The fluidic chip device according to claim 1, wherein a shape and a surface area of the two outer boundary layers match to a shape and to a surface area of the at least two reinforcing layers.

14. The fluidic chip device according to claim 1, comprising a processing element arranged in the fluidic conduit and configured for interacting with the fluidic sample.

15. The fluidic chip device according to claim 1, wherein the at least two reinforcing layers are laminated with the directly adjacent layers without being connected to each other.

16. A method of fabricating a fluidic chip device for processing a fluidic sample, the method comprising:
    arranging at least two reinforcing layers between two outer boundary layers, the at least two reinforcing layers having a mechanical resistance larger than a mechanical resistance of the two outer boundary layers;
    laminating each of the at least two reinforcing layers at both of its opposing main surfaces with directly adjacent layers to reinforce pressure resistance of the fluidic chip device by the lamination; and
    arranging a core layer between at least one of the at least two reinforcing layers, wherein the core layer is laminated with the at least two reinforcing layers, and comprises a hole forming at least a part of a fluidic conduit for conducting the fluidic sample under pressure.

17. The method according to claim 16, wherein at least one of the at least two reinforcing layers is roughened before being connected to the adjacent layers.

18. The method according to claim 16, comprising functionalizing at least one layer before laminating the functionalized layer to another layer, the functionalized layer being selected from the group consisting of: at least one of the at least two reinforcing layers, at least one of the adjacent layers, and a combination of two or more of the foregoing.

19. The method according to claim 16, wherein at least one of the at least two reinforcing layers is cleaned using a chemical cleaner in an ultrasound bath before being connected to the adjacent layers.

20. The method according to claim 16, wherein the at least two reinforcing layers are laminated with the directly adjacent layers without being connected to each other.

* * * * *